(12) United States Patent
Sommer et al.

(10) Patent No.: US 8,332,051 B2
(45) Date of Patent: *Dec. 11, 2012

(54) HIGH IMPEDANCE ACTIVE FIXATION ELECTRODE OF AN ELECTRICAL MEDICAL LEAD

(75) Inventors: John L. Sommer, Coon Rapids, MN (US); Daniel C. Sigg, St. Paul, MN (US); James A. Coles, Jr., Columbia, MD (US)

(73) Assignee: Medtronic, Inc., Minneapolis, MN (US)

( * ) Notice: Subject to any disclaimer, the term of this patent is extended or adjusted under 35 U.S.C. 154(b) by 328 days.

This patent is subject to a terminal disclaimer.

(21) Appl. No.: 12/782,465

(22) Filed: May 18, 2010

(65) Prior Publication Data

US 2010/0292768 A1 Nov. 18, 2010

Related U.S. Application Data

(63) Continuation of application No. 11/004,744, filed on Dec. 3, 2004, now Pat. No. 7,720,550.

(51) Int. Cl.
*A61N 1/00* (2006.01)
(52) U.S. Cl. .................................................. 607/127
(58) Field of Classification Search .................. 607/127
See application file for complete search history.

(56) References Cited

U.S. PATENT DOCUMENTS

| | | | |
|---|---|---|---|
| 3,416,534 A | 12/1968 | Quinn | |
| 3,472,234 A | 10/1969 | Tachick | |
| 3,737,579 A | 6/1973 | Bolduc | |
| 4,000,745 A | 1/1977 | Goldberg | |
| 4,010,758 A | 3/1977 | Rockland et al. | |
| 4,026,303 A | 5/1977 | Babotai | |
| 4,282,885 A | 8/1981 | Bisping | |
| 4,313,448 A | 2/1982 | Stokes | |
| 4,506,680 A | 3/1985 | Stokes | |
| 4,577,642 A | 3/1986 | Stokes | |
| 4,606,118 A | 8/1986 | Cannon et al. | |
| 4,662,382 A | 5/1987 | Sluetz et al. | |
| 4,711,251 A | 12/1987 | Stokes | |
| 4,762,136 A | 8/1988 | Baker, Jr. | |
| 5,143,090 A | 9/1992 | Dutcher et al. | |
| 5,246,014 A | 9/1993 | Williams et al. | |
| 5,282,844 A | 2/1994 | Stokes et al. | |
| 5,324,325 A | 6/1994 | Moaddeb | |
| 5,531,783 A | 7/1996 | Giele et al. | |

(Continued)

FOREIGN PATENT DOCUMENTS

EP 0 042 551 B1 11/1984

(Continued)

*Primary Examiner* — Mark W Bockelman
(74) *Attorney, Agent, or Firm* — Reed A. Duthler (57) ABSTRACT

Electrical medical leads having active fixation electrodes, particularly helix electrodes intended to be screwed into body tissue, e.g., the heart, are disclosed having selectively applied insulation to optimize exposed electrode surface area and dispose the exposed electrode surface area toward tissue that is less traumatized by injury caused by screwing in the fixation helix. In a preferred fabrication method, an outer helical surface is masked by contact with a masking tube while a dielectric coating is applied to the inner helical surface of the coil turns of the helix, and the masking tube is removed when the dielectric coating has set. In one variation, at least one aperture is formed through the masking tube sidewall exposing an area of the outer helical surface thereby interrupting the uninsulated outer helical electrode.

19 Claims, 4 Drawing Sheets

U.S. PATENT DOCUMENTS

| | | | |
|---|---|---|---|
| 5,575,814 A | 11/1996 | Giele et al. | |
| 5,837,006 A | 11/1998 | Ocel et al. | |
| 5,902,324 A | 5/1999 | Thompson et al. | |
| 5,987,746 A | 11/1999 | Williams | |
| 6,078,840 A | 6/2000 | Stokes | |
| 6,108,582 A | 8/2000 | Fischer, Sr. | |
| 6,298,272 B1 | 10/2001 | Peterfeso et al. | |
| 6,321,122 B1 | 11/2001 | Scheiner et al. | |
| RE37,463 E | 12/2001 | Altman | |
| 6,408,214 B1 | 6/2002 | Williams et al. | |
| 6,478,776 B1 | 11/2002 | Rosenman et al. | |
| 6,501,994 B1 | 12/2002 | Janke et al. | |
| 6,526,321 B1 | 2/2003 | Spehr | |
| 7,027,876 B2 | 4/2006 | Casavant et al. | |
| 7,212,870 B1 | 5/2007 | Helland | |
| 7,720,550 B2 * | 5/2010 | Sommer et al. | 607/127 |
| 2001/0020179 A1 | 9/2001 | Audoglio | |
| 2003/0060868 A1 | 3/2003 | Janke et al. | |
| 2003/0163184 A1 | 8/2003 | Scheiner et al. | |
| 2003/0204233 A1 | 10/2003 | Laske et al. | |
| 2005/0070985 A1 | 3/2005 | Knapp et al. | |
| 2005/0131509 A1 | 6/2005 | Atanassoska et al. | |

FOREIGN PATENT DOCUMENTS

WO     WO 99/30772 A3     6/1999

* cited by examiner

HIGH IMPEDANCE ACTIVE FIXATION ELECTRODE OF AN ELECTRICAL MEDICAL LEAD

RELATED APPLICATION

This application is a continuation of U.S. patent application Ser. No. 11/004,744, filed Dec. 3, 2004 entitled "High Impedance Active Fixation Electrode Of An Electrical Medical Lead", herein incorporated by reference in its entirety.

TECHNICAL FIELD

The present invention relates to electrical medical leads having active fixation electrodes, particularly helix electrodes intended to be screwed into body tissue, e.g., the heart, having selectively applied insulation to optimize exposed electrode surface area and dispose the exposed electrode surface area toward tissue that is less traumatized by injury caused by screwing in the fixation helix.

BACKGROUND

Implantable medical electrical stimulation and/or sensing leads (electrical medical leads) are well known in the fields of tissue stimulation and monitoring, including cardiac pacing and cardioversion/defibrillation, and in other fields of electrical stimulation or monitoring of electrical signals or other physiologic parameters. In the field of cardiac stimulation and monitoring, the electrodes of epicardial or endocardial cardiac leads are affixed against the epicardium or endocardium, respectively, or inserted therethrough into the underlying myocardium of the heart wall.

Epicardial or myocardial cardiac leads, or simply epicardial leads, are implanted by exposure of the epicardium of the heart typically through a limited thorocotomy or a more extensive surgical exposure made to perform other corrective procedures. Endocardial cardiac leads, or simply endocardial leads, are implanted through a transvenous route to locate one or more sensing and/or stimulation electrode along or at the distal end of the lead in a desired implantation site in a chamber of the heart or a blood vessel of the heart. It is necessary to accurately position the electrode surface against the endocardium or within the myocardium or coronary vessel at the implantation site.

A passive or active fixation mechanism is typically incorporated into the distal end of permanent cardiac leads and is deployed at the implantation site to maintain the distal end electrode in contact with the endocardium or within the myocardium. Considerable effort has been undertaken to develop passive and active fixation mechanisms that are simple to use and are reliable in maintaining the distal electrodes in position.

Active fixation mechanisms are designed to penetrate the epicardial or endocardial surface and lodge in the myocardium without perforating all the way through the myocardium. The most widely used active fixation mechanism employs a helix, which typically also constitutes a pace/sense electrode. Typically, a mechanism is used to shield the sharpened tip of the helix during the transvenous advancement into the desired heart chamber or coronary vessel or to the epicardial surface. In one approach, a retraction mechanism that retracts the helix into a distal cavity of the lead body as shown in U.S. Pat. Nos. 5,837,006 and 6,298,272, for example, is employed. In another approach, a shroud, e.g., a plug of dissolvable biocompatible material as disclosed in U.S. Pat. No. 5,531,783, for example, is applied over and between the coil turns of the helix. In still another approach, the lead is introduced through the sheath of a guide catheter, as disclosed in U.S. Pat. No. 6,408,214, for example, that is advanced to the implantation site. The helix is advanced from the sheath or out of the lead body or the plug dissolves when the desired implantation site is reached. In one manner or another, the helix is adapted to be rotated by some means from the proximal end of the lead body outside the patient's body in order to screw the turns of the helix into the myocardium and permanently fix the pace/sense electrode.

Over the last 30 years, it has become possible to reduce endocardial lead body diameters from 10 to 12 French (3.3 to 4.0 mm) down to 2 French (0.66 mm) presently through a variety of improvements in conductor and insulator materials and manufacturing techniques. The lead bodies of such small diameter, 2 French, endocardial leads are formed without a lumen that accommodates use of a stiffening stylet to assist in implantation.

Such a small diameter endocardial lead is formed with an active fixation helix that extends distally and axially in alignment with the lead body to a sharpened distal tip and that has a helix diameter substantially equal to the lead body diameter. The fixation helix does not necessarily increase the overall diameter of the endocardial lead, and fixation is relatively robust once the helix is screwed into the myocardium. Typically, but not necessarily, the fixation helix is electrically connected to a lead conductor and functions as a pace/sense electrode. In some cases, the lead body encloses one or more helical coiled or stranded wire conductor and lacks a lumen.

When the fixation helix is used as a pace/sense electrode, the surface area of the fixation helix must be controlled within a range that historically has been between 6-10 $mm^2$, typically 8 $mm^2$. The fixation helix outer diameter approximates the lead body diameter, and the fixation helix typically has more than one coil turn. More recent, small diameter fixation helices have surface areas in the range of 2.0 $mm^2$ to 5.0 $mm^2$ typically 4.0 $mm^2$. The number of turns and length of the fixation helix is selected to avoid perforation through the heart wall. The exposed electrode surface must be within the myocardium rather than exposed outside the heart or inside a heart chamber.

Consequently, it is conventional to coat a part or parts of the fixation helix with electrical insulation to control the exposed surface area and to ensure that the exposed portion of the helix remains within the myocardium when the helix is properly screwed in. See, for example, U.S. Pat. Nos. 4,000,745, 4,010,758, 5,143,090, and 6,501,994 and U.S. Patent Application Publication Nos. 2003/0060868 and 2003/0163184. Electrically insulating coatings are also applied to portions of barbed electrodes of epicardial leads as shown, for example in commonly assigned U.S. Pat. No. 4,313,448. Electrical insulation of a fixation helix that is not employed as a pace/sense electrode is shown, for example, in U.S. Pat. No. 4,662,382. Various forms of selective electrical insulation of other shapes of pace/sense electrodes are shown in U.S. Pat. Nos. 4,026,303 and 6,526,321 and in EP Publication No. 0 042 551.

The dielectric, biocompatible, insulating coatings of choice have included silicone rubber and non-thrombogenic compounds such as Parylene™ parylene, and various polyurethanes, polyacrylates (including polymethacrylates), polyesters, polyamides, polyethers, polysiloxanes, polyepoxide resins and the like. Cross-linked polymers within these classes may be preferred for their resistance to breakdown and their physical durability. Parylene coatings on the surfaces of implantable medical devices have been widely accepted, and the deposition of a parylene coating on a pace/ sense electrode can be readily effected using a parylene vacuum deposition system that delivers poly-paraxylylene into a vacuum chamber containing the targeted electrode. The portions of the deposited parylene coating can be etched away as disclosed in the above-referenced '321 patent to expose the pace/sense electrode surface.

The ideal electrode impedance for chronic pacing across the electrode-tissue interface is in the range of 800 to 1,000 ohms. For example, the impedances reported in the above-referenced '994 patent are about 800 ohms measured during chronic implantation. The perforation of the myocardium by the fixation helix causes inflammation and cell death, particularly of myocardial cells between the turns of the helix and within the helix lumen, and impedance rises for a time following implantation to about 1200 ohms, for example, before falling to the chronic impedance level. Cell death and substitution of scar tissue for excitable myocardial cells is responsible for the observed impedance changes. Steroid eluting coatings and devices are commonly incorporated into the distal end of the lead body to counter post-implantation impedance rise as described in the above-referenced '994 patent and in U.S. Pat. No. 5,324,325, for example.

Pace/sense electrodes are typically formed of platinum or platinum iridium alloys that are bio-compatible and bio-stable during chronic implantation and delivery of pacing pulses. Consequently, fixation helices used as pace/sense electrodes are formed of platinum or platinum iridium wire wound into the helical shape to have one or more coil turn terminating in a sharpened tip. It is also common practice to surface treat or etch the electrode surface area of helical screw-in electrodes or to coat the electrode surface area with platinum black or a platinum metal oxide to create a surface texture that enhances the characteristics of the tissue-electrode interface to decrease post pulse delivery polarization and stabilizes impedance changes, as disclosed in U.S. Pat. No. 4,762,136, for example.

It is not convenient to surface treat the fixation helix, coat the surface treated helix with a dielectric insulating layer, and then selectively etch away the insulating layer to expose the pace/sense electrode surface as suggested in the above-referenced '321 patent, since the etching may damage an electrode coating or surface treatment.

Moreover, the selective insulation techniques and resulting electrode surface areas on pace/sense screw-in electrodes disclosed in the prior art fail to address the injury and cell death occurring within the lumen of the fixation helix.

SUMMARY

The methods of fabrication of fixation helices of the present invention address these issues and provides a fixation helix having selectively applied insulation to optimize exposed electrode surface area and dispose the exposed electrode surface area toward tissue that is less traumatized by injury caused by screwing the fixation helix into the tissue. The methods of the present invention may be applied to any of the above-described helices of endocardial and epicardial leads.

A preferred embodiment of a fixation helix of the present invention has at least one turn, wherein an inner spiral or helical surface is electrically insulated and an outer spiral or helical surface is exposed to function as a pace/sense electrode exposed to myocardial cells surrounding the turns of the helix.

In a preferred fabrication method, the outer helical surface is masked when a dielectric coating is applied to the inner helical surface, and the masking is removed when the dielectric coating has set. In one approach, the helix is fitted into the lumen of a resilient masking tube such that the lumen surface bears snugly against the outer helical surface of the helix. The dielectric material is directed into the coaxially aligned helix lumen and tube lumen and forms a dielectric coating on the inner helical surface of the coil turns of the helix. The resilient masking tube is then removed, as by slitting through the tubing sidewall and peeling the tubing from the helix to expose the uncoated outer helical surface.

In one variation, at least one aperture is formed through the masking tube side wall exposing an area of the outer helical surface. The uninsulated outer helical electrode is thereby rendered non-continuous through its length.

Advantageously, the entire surface of the fixation helix may be surface treated in any of the conventional ways or coated with any of the conventional materials for optimizing impedance, reducing polarization, reducing inflammation, and enhancing the electrode-tissue interface before the helix is fitted into the lumen of the masking tube. The surface treatment or coating is not damaged by contact with the masking tube during deposition of the dielectric layer. Alternatively, the uninsulated outer helical electrode surface may be treated or coated following deposition of the insulating material.

Furthermore, the entire surface of the fixation helix or the insulated surface of the fixation helix may be coated with or incorporate a steroid. The exposed outer helical electrode is directed toward viable, excitable myocardial cells, and battery energy can be conserved due to as pacing energy is directed away from traumatized cells within the helix lumen and between the spiral turns. The exposed electrode surface area can be substantially reduced even for a small diameter fixation helix to achieve an optimal impedance due to the outward orientation of the outer helical electrode surface that avoids delivering stimulation energy to traumatized tissue or myocardial cells within the helix lumen or between the adjacent facing surfaces of the coil turns.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be readily appreciated as the same becomes better understood by reference to the following detailed description when considered in connection with the accompanying drawings, in which like reference numerals designate like parts throughout the figures thereof and wherein.

The drawing figures are not necessarily to scale.

DETAILED DESCRIPTION

In the following detailed description, references are made to illustrative embodiments for carrying out the invention. It is understood that other embodiments may be utilized without departing from the scope of the invention. The invention and its preferred embodiments may be employed in unipolar, bipolar or multi-polar, endocardial, cardiac pacing leads, cardioversion/defibrillation leads or monitoring leads having at least one pace/sense electrode formed as part of the distal fixation helix that is to be screwed into the myocardium. It will be understood that other sensors for sensing a physiologic parameter may be incorporated into the lead body.

An insulated electrical conductor extending proximally through the lead body to connector element of a lead proximal end connector assembly is coupled to each such pace/sense electrode, sense electrode, cardioversion/defibrillation electrode and sensor. The proximal connector assembly is adapted to be coupled to the connector assembly of an external medical device, including an external pacemaker or monitor, or an implantable medical device, including an implantable pulse generator (IPG) for pacing, cardioversion/defibrillation (or both) or an implantable monitor.

The methods of the present invention are particularly useful in optimizing electrode surface area on the distal fixation helix to provide optimal pacing and sensing impedance and to dispose the exposed electrode surface area toward myocardial tissue that is less traumatized by injury caused by screwing the fixation helix into the myocardium.

The cardiac lead of the preferred embodiment of the invention can be introduced in a variety of ways to the epicardial or endocardial surface of the heart or into a coronary blood vessel so that the distal fixation helix can be screwed into the myocardium. Epicardial implantation sites, particularly left ventricular sites can be accessed in a variety of ways involving surgical creation of a thoracic passage and use of an introducer and guide catheter. Endocardial implantation sites include the apex of the right ventricle, the atrial appendage or at other sited of the right atrium, and into the coronary sinus.

Figure 1:
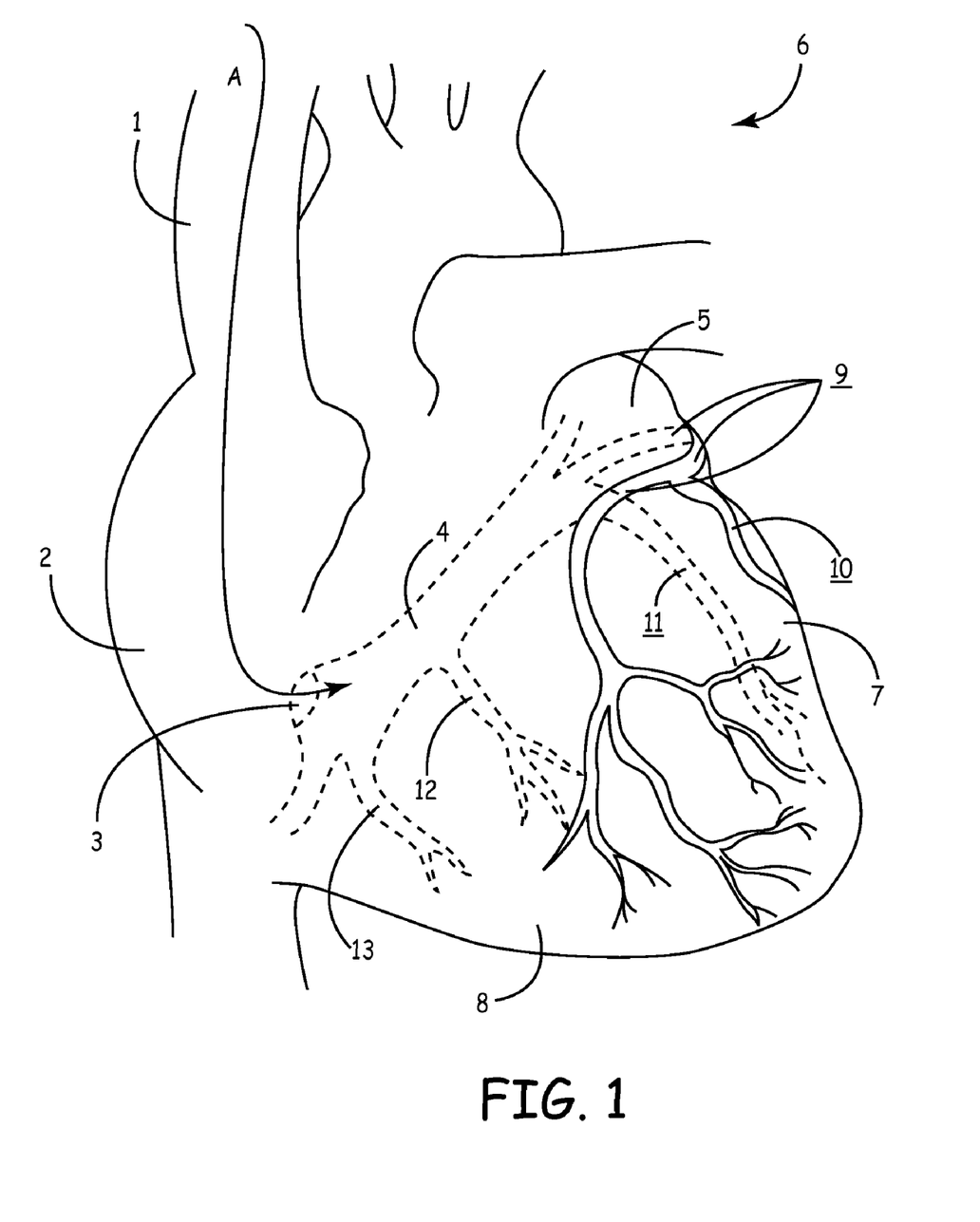
FIG. 1 is a schematic diagram of a heart from an anterior perspective illustrating the coronary venous system about an epicardial surface of the heart, including dashed lines depicting a portion of coronary venous system on an opposite, posterior epicardial surface of the heart.

For convenience, exemplary endocardial implantation sites are depicted in FIG. 1, particularly sites within the coronary sinus and vessels branching therefrom. FIG. 1 is a schematic diagram of a heart 6 from an anterior perspective illustrating a coronary venous system about an epicardial surface, including dashed lines depicting a portion of coronary venous system on an opposite, posterior surface of the heart 6. FIG. 1 also illustrates a pathway, defined by arrow 'A', which may be followed in order to place a cardiac lead within CS 4, extending from a venous access site (not shown) through the superior vena cava (SVC) 1 into the right atrium (RA) 2 of heart 6 and from the RA 2 into the CS 4 through a coronary sinus ostium (CS Os) 3.

As illustrated in FIG. 1, the coronary venous system of a heart 6 includes the CS 4 and vessels branching therefrom including the middle cardiac vein (MCV) 13, the posterior cardiac vein (PCV) 12, the posterior-lateral cardiac vein (PLV) 11, the great cardiac vein (GCV) 9, and the lateral cardiac vein (LCV) 10 all branching away from the CS 4. Generally speaking, the distal portion of the CS 4 and the branching vessels including at least portions of the MCV 13, PCV 12, the PLV 11, the GCV 9, and the LCV 10 overlie the or are embedded within the epicardium that defines outer surface of the heart 6 and encases heart muscle or myocardium. Portions of the epicardium are spaced from a surrounding pericardial sac or pericardium (not shown), whereby a pericardial space surrounds the spaced epicardium of heart 6. Thus, the vessel walls of the distal portion of the CS 4 and the branching vessels including at least portions of the MCV 13, PCV 12, the PLV 11, the GCV 9, and the LCV 10 are partially exposed to the pericardial space or adhered to the pericardium and are partially embedded against the underlying myocardium. For convenience of terminology, the vessel walls that are disposed toward the pericardium are referred to as disposed "away from the heart", whereas the vessel walls that are disposed toward the myocardium are referred to as disposed "toward the heart".

In patients suffering from heart failure, a CS lead of the types described above is advanced through the pathway "A" extending through the SVC 1 and RA 2 into the CS 4 to dispose one or a pair of distal pace/sense electrodes at an LV site(s) within one of the vessels branching from the CS 4. An RV lead is advanced through the SVC 1, the RA 2, the tricuspid valve, and the distal pace/sense electrode(s) is affixed at an RV pace/sense site(s) of the RV 8, e.g., in the RV apex or along the septum separating the RV and LV chambers. The RV lead can take any of the functions known in the art preferably having an active or passive fixation mechanism.

The proximal connectors of the CS lead and the RV lead are coupled to a connector header of a pacing IPG or an ICD IPG (not shown) implanted subcutaneously. The IPG is capable of sensing and processing cardiac signals detected at the pace/sense site(s) to provide synchronized RV and LV pacing at the pace/sense sites as needed. The pacing and sensing functions of such an IPG that provides synchronous activation of the RV 8 and LV 7 in order to improve the hemodynamic output of the heart 6 are disclosed in commonly assigned U.S. Pat. No. 5,902,324, for example, and are embodied in the MEDTRONIC® InSync Marquis™ ICD IPG, for example.

Hemodynamic output is enhanced when the CS pace/sense electrode(s) site is selected within a late activated region of LV 7. Late activated regions of the LV 7 are found within the myocardium underlying the PLV 11, the LCV 10, the GCV 9, or the CS 4 near a junction with the GCV 9. Moreover, pacing and sensing functions are optimized when the pace/sense electrode(s) are disposed in intimate contact with excitable myocardial tissue. Thus, the CS pace/sense electrode(s) are to be advanced through the pathway "A" to the site of a selected late activated region and affixed so that the CS pace/sense electrodes are disposed toward the heart 6 and not disposed away from the heart 6. The fixation is accomplished by use of an active fixation helix that is directed toward the heart 6 and screwed through the vessel wall and into the myocardium.

The lead body of an endocardial lead introduced to a fixation site within the RA 2, the RV 8, and the CS 4, and vessels branching therefrom, typically comprises one or more insulated conductive wire surrounded by an insulating outer sheath. Each conductive wire couples a proximal lead connector element with a distal stimulation and/or sensing electrode. Epicardial and endocardial leads having a single stimulation and/or sensing electrode at the lead distal end, a single conductor, and a single connector element are referred to as unipolar leads. Epicardial and endocardial leads having two or more stimulation and/or sensing electrodes at the lead distal end, two or more respective conductors, and two or more respective connector elements are referred to as bipolar leads or multi-polar leads, respectively.

Figure 2:
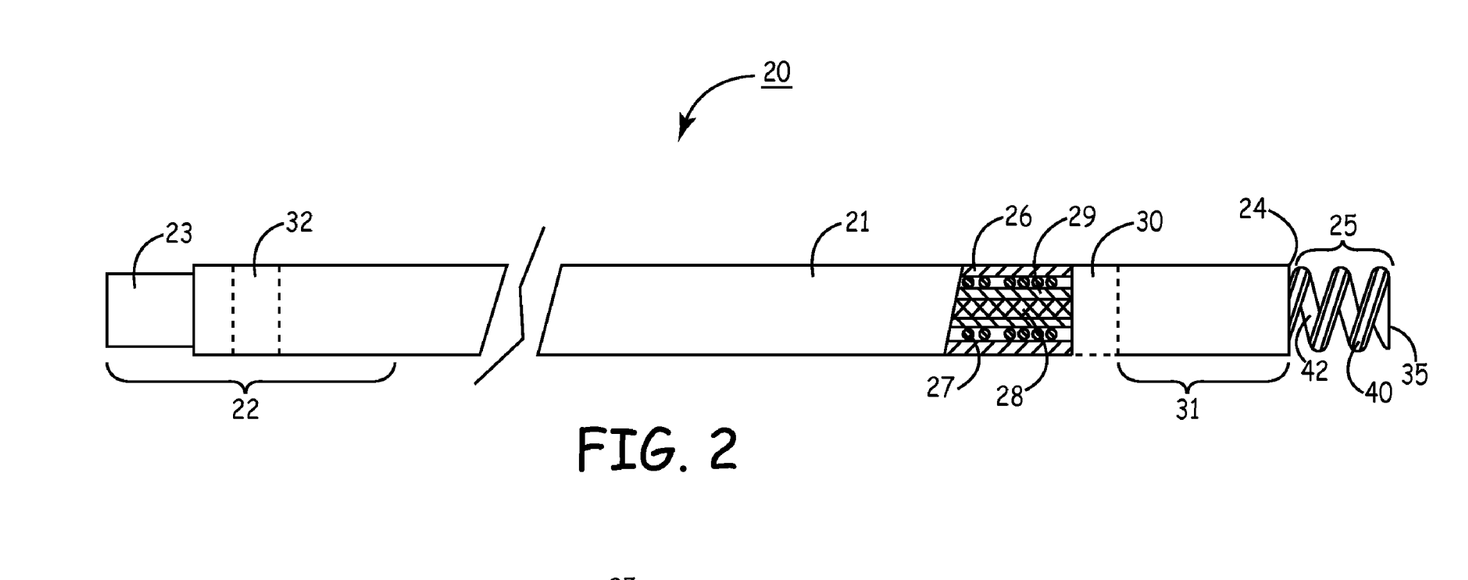
FIG. 2 is a plan view, in partial exposed section, of a pacing lead having a distal fixation helix functioning as a pace/sense electrode and having selectively applied insulation to optimize exposed electrode surface area and dispose the exposed electrode surface area toward myocardial tissue that is less traumatized by injury caused by screwing the fixation helix into the myocardium.

A typical example of an active fixation cardiac lead 20 in which the present invention is implemented is schematically illustrated in FIG. 2. The cardiac lead 20 has an elongated lead body 21 that extends between a proximal connector 22 and a distal end 24. A helical fixation element or helix 25 having a sharpened piercing tip 251 extends distally from lead body distal end 24. The cardiac lead 20 can be configured as a unipolar or a bipolar or multi-polar lead for both endocardial or epicardial implantation. The distal fixation helix 25 of the cardiac lead can be affixed into the myocardium at any site of the RA 2 or the RV 8, or any site accessed by advancement through pathway "A" into the CS or vessels branching therefrom. In addition, the cardiac lead 20 can be introduced to an epicardial implantation site in the manner described above, for example.

Pacing lead 20 is essentially iso-diametric along its length, with an outer diameter of lead body 21 and fixation helix 25 between approximately 1 French (0.33 mm) to 3 French (1.00 mm). Since lead body 21 does not include an inner lumen, the outer diameter of lead body 21 is reduced in this example. However, it will be understood that the features of the present invention can be employed with lead bodies that include one or more lumen.

In this example depicted in FIG. 2, lead body 21 is constructed of a stranded conductive or non-conductive filament cable 28 disposed within an inner sheath lumen of an inner sheath 29, which in turn extends through the coil lumen of a coil 27. The assembly of the coil 27, inner sheath 29, and cable 28 is fitted through an outer sheath lumen of an outer sheath 26.

Coil 27 is formed of any bio-stable and biocompatible material that is sufficiently stiff to provide adequate torque transfer from proximal connector assembly 22 to fixation element 25 at distal end 24 of cardiac lead 20. When coil 27 functions as a lead conductor, coil 27 is preferably formed of single or multiple wire filars made of MP35-N alloy, well known in the art, or any other bio-stable and biocompatible material that is capable of reliably conducting electrical current after having been subjected to numerous, repeated bending and torsional stresses.

Inner cable 28 is formed from synthetic filaments or conductive metallic wires, when inner cable functions as a lead conductor. The proximal and distal ends of inner cable 28 are coupled to connector pin 23 or within connector assembly 22 and fixation helix 25, respectively, to provide tensile strength to lead body 21.

Outer sheath 26 is formed of either a silicone rubber or polyurethane, well known in the art, or any other flexible, bio-stable and biocompatible, electrically insulating, polymer material. Inner sheath 29 is similarly formed of a bio-stable and biocompatible flexible polymer coating or tube that protects inner cable 28 from mechanical stresses or hydrolytic degradation and electrically insulates inner cable 28 from contact with wire coil 27. Inner sheath 29 can be formed of flexible, bio-stable and biocompatible electrically insulating materials known in the art, including silicone rubber compounds, polyurethanes, and fluoropolymers.

In both unipolar and bipolar cardiac lead embodiments, the proximal connector assembly 22 includes a connector pin 23 that is typically electrically connected with the distal fixation helix 25 when the distal fixation helix 25 functions as a pace/sense electrode. In a bipolar cardiac lead embodiment, the proximal connector assembly 22 includes a connector ring 32 (shown with dashed lines) that is electrically coupled to a ring-shaped pace/sense electrode 30 (shown with dashed lines) supported by outer sheath 26 proximal to fixation helix 25. The connector assembly 22 is shaped to be inserted into a bore of a connector block of the connector header of an IPG as described above to make an electrical connection between the distal pace/sense electrode(s) and IPG sensing and/or pacing pulse generating circuitry. The fixation helix 25 is adapted to be screwed into the myocardium, as described below, by rotation of lead body 21 from the proximal connector assembly 22 when piercing tip 251 is advanced to and oriented toward a fixation site.

In a unipolar embodiment of cardiac lead 20, the inner cable 28 is nonconductive, a proximal end of coil 27 is coupled to connector pin 23, and a distal end of coil 27 is coupled to the proximal end of fixation helix 25. The proximal and distal ends of coil 27 are welded or crimped to the connector pin 23 and fixation helix 25, respectively, using common welding or crimping techniques known in the art. The proximal and distal ends of inner cable 28 are crimped to the connector pin 23 or connector assembly 22 and fixation helix 25, respectively, using common welding or crimping techniques known in the art.

In an alternate unipolar embodiment wherein the inner cable is nonconductive, helix fixation element 25 simply provides fixation and does not function as a pace/sense electrode. The proximal end of coil 27 is coupled to connector pin 23, and the distal end of coil 27 is coupled to the ring-shaped pace/sense electrode 30 incorporated coaxially about a distal portion of lead body 21. The spacing 31 between ring-shaped pace/sense electrode 30 and fixation helix 25 is less than approximately 0.02 inches in order to locate ring-shaped pace/sense electrode 30 close enough to a fixation site for tissue contact when fixation helix 25 is fixed into the myocardium.

In a further alternate unipolar embodiment of cardiac lead 20, inner cable 28 is electrically conductive, and the proximal and distal cable ends are electrically coupled by crimping or welding or other known techniques to connector pin 23 and helix fixation element 25, respectively. Inner sheath 29 electrically insulates inner cable 28 from coil 27, which acts only as a structural element to provide torsional stiffness to lead body 21. Alternatively, the proximal and distal ends of the conductive inner cable 28 and the wire coil 27 can be electrically connected together to provide a redundant unipolar lead conductors. Conductive inner cable 28 is preferably formed from wire strands or filaments made of MP35-N alloy, well known in the art, or any other bio-stable and biocompatible material that is capable of reliably conducting electrical current after having been subjected to numerous, repeated bending and torsional stresses.

In a bipolar embodiment of cardiac lead 20, both coil 27 and inner cable 28 are lead conductors as described above, that are electrically insulated from one another by inner sheath 29. The ring-shaped pace/sense electrode 30 is preferably formed of a platinum alloy but other materials may also be used, including but not limited to such materials as palladium, titanium, tantalum, rhodium, iridium, carbon, vitreous carbon and alloys, oxides and nitrides of such metals or other conductive or even semi-conductive materials. Of course, some materials are incompatible with others and may not be effectively used together. The limitations of specific materials for use with others are well known in the art. The proximal and distal ends of coil 27 are electrically and mechanically coupled by crimping or welding to the connector ring 32 and the ring-shaped pace/sense electrode 30, respectively. The proximal and distal ends of the inner cable 28 are electrically and mechanically coupled by crimping or welding to connector pin 23 and distal fixation helix 25, respectively.

The spacing 31 between ring-shaped pace/sense electrode 30 and fixation helix 25 is between approximately 0.2 inches and 0.4 inches, a range well known in the pacing art for inter-electrode bipolar pace/sense electrode spacing.

The exemplary active fixation cardiac lead 20 can also be formed having an elongated cardioversion/defibrillation (C/D) electrode extending proximally a predetermined distance along the outer sheath 21 from a C/D electrode distal end located proximal to distal lead end 24. The proximal and distal ends of the wire coil 27 would be electrically and mechanically coupled to the connector ring 32 and the elongated C/D electrode, respectively. The proximal and distal ends of the inner cable 28 would be electrically and mechanically coupled by crimping or welding to connector pin 23 and distal fixation helix 25, respectively.

A means for steroid elution may be incorporated into any of the aforementioned embodiments of the exemplary active fixation cardiac lead 20 near distal end 24 to counter post-implantation impedance rise. Such steroid elution means may take the form of a monolithic controlled release device (MCRD), preferably constructed from silicone rubber and loaded with a derivative of dexamethasone, such as the water-soluble steroid dexamethasone sodium phosphate. MCRD construction and methods of fabrication are found in commonly assigned U.S. Pat. Nos. 4,506,680, 4,577,642, 4,606,118, 4,711,251, and 5,282,844. Alternatively a steroid coating containing a no more than sparingly water-soluble steroid such as beclomethasone diproprionate or dexamethasone acetate may be applied to surfaces of ring-shaped pace/sense electrode 30 and/or fixation helix 25. A steroid coating composition and method of application is found in commonly assigned U.S. Pat. No. 5,987,746. The steroid coating may be applied directly to surfaces or portions of surfaces preserving structural integrity of ring-shaped pace/sense electrode 30 and/or fixation helix 25 and taking up less space than an MCRD.

Such an exemplary active fixation cardiac lead 20 can be employed advantageously as a CS lead through the use of a guide catheter advanced through the pathway "A" of FIG. 1 to locate the fixation helix 25 at a fixation site in the coronary vasculature and to aim the helix tip 251 toward the heart before the connector assembly 22 is rotated to screw the fixation helix 25 through the vessel wall and into the myocardium.

In one approach shown, for example, in commonly assigned U.S. Pat. Nos. 5,246,014 and 6,408,214, the lead body is enclosed within the lumen of a further sheath or introducer, and the lead and introducer are disposed within the lumen of the guide catheter. The fixation helix is located within the catheter lumen during advancement of the lead distal end fixation helix through the transvenous pathway and heart chamber or coronary vessel to dispose the fixation helix near the implantation site.

Similar approaches have been undertaken to advance a fixation helix through minimally invasive surgical exposure of the pericardial sac to the epicardium of the heart and to screw the fixation helix into the myocardium. Early examples of such epicardial screw-in leads are shown, for example, in U.S. Pat. Nos. 3,472,234, 3,416,534, 3,737,579, 4,000,745, and 4,010,758, for example.

As shown in FIG. 2, the fixation helix 25 extends from a helix attachment end to a distal end terminating in a helix tip 35 shaped to penetrate body tissue when the helix 25 is screwed into body tissue to secure fixation to the implantation site. In accordance with the present invention, the fixation helix 25 is fabricated following the exemplary method depicted in FIGS. 3-8 or the variation method depicted in FIGS. 9-12 having a layer or coating 42 or 142 of insulating material covering at least a portion of an inner helical surface of each coil turn disposed toward the helix lumen. After the coating 42 or 142 is applied, at least a portion of an uncoated outer helical surface of each coil turn comprises an uninsulated outer helical electrode 40 or 140. The outer helical electrode 40 or 140 is disposed toward body tissue away from the helix lumen to function as a stimulation and sensing electrode upon implantation.

Figure 3:
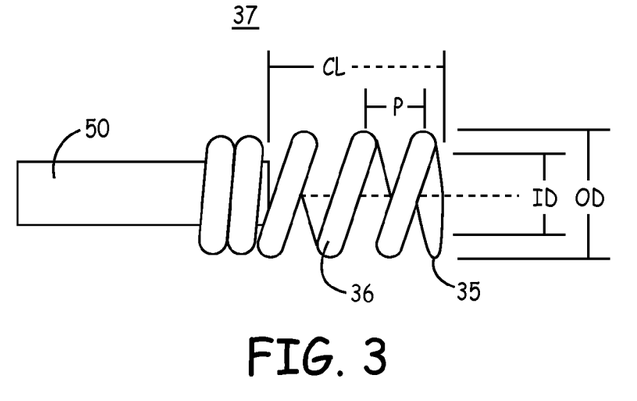
FIG. 3 is a plan view of the distal fixation helix mounted for surface coating prior to assembly to the lead body of the pacing lead of FIG. 2.
Figure 4:
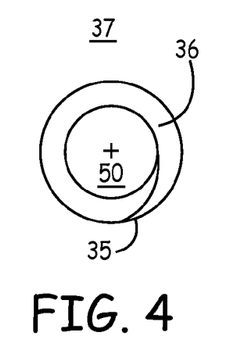
FIG. 4 is an end view of the distal fixation helix of FIG. 3.

When fixation helix 25 functions as a pace/sense electrode of a pacing lead, as in any of the alternate endocardial and epicardial, unipolar and bipolar or multi-polar embodiments described above, fixation helix 25 is preferably formed of a platinum iridium alloy wire 36 shown in FIG. 3. It is understood that other biocompatible and bio-stable materials may also be used to form wire 36, including but not limited to such materials as palladium, titanium, tantalum, rhodium, carbon, vitreous carbon and alloys, oxides and nitrides of such metals or other conductive or even semi-conductive materials well known in the art.

As shown in FIG. 3, the conductive wire 36 is preferably formed into a coil 37 comprising at least one coil turn (in this example, about three turns) wound to define a helix lumen within the inner diameter ID of the coil turns. The coil 37 extends from a support used during helix fabrication or a crimp tube 50 that will be used to attach the fixation helix 25 to the distal end of a conductor within the lead body. The coil 37 is wound about the crimp tube 50, in this example, so that fixation helix attachment end is formed. The free end of the coil 37 is shaped to form the helix tip 35 that penetrates body tissue when the helix 25 is screwed into body tissue to secure fixation to the implantation site. Thus, a plurality of coil turns are depicted in FIG. 3 that are space wound through a coil length CL in a constant pitch P and coil outer diameter OD defining the helix outer diameter and a coil inner diameter ID defining the helix lumen diameter. The space winding ensures that a space exists between facing surfaces of adjacent coil turns.

In one preferred embodiment, the wire 36 has a diameter of 0.25 mm, the pitch P is 1.0 mm, the coil OD is 1.6 mm, the coil ID is 1.1 mm and the coil length CL is 1.8 mm providing a helix surface area of 4.2 mm$^2$. These dimensions can be varied to provide helix surface areas in the range of 2.0 mm$^2$ to 10.0 mm$^2$. The present invention can be employed to selectively reduce the electrode surface area of a relatively large diameter fixation helix that provides robust fixation while advantageously orienting the electrode surface area toward viable, excitable body tissue at an implantation site. For example, the electrode surface area of a fixation helix having a total surface area of about 4.2 mm$^2$ can be selected to be between about 0.8 mm$^2$ to 2.1 mm$^2$. About 10% to about 50% of the surface area helix surface area can be coated in accordance with the present invention.

The surface of the coil turns of the wire 36 is preferably surface treated or coated with a coating selected from the group consisting of titanium nitride, iridium oxide, platinum black, and carbon nanotubes to create a surface texture that enhances the characteristics of the tissue-electrode interface to decrease post pulse delivery polarization and stabilizes impedance changes. Advantageously, the coating or surface treatment can be done prior to application of the coating 42 of insulating material on the inner helical surface as described further below. Alternatively, the coating or surface treatment on the uninsulated outer helical electrode 40 can be done following application of the coating 42 of insulating material on the inner helical surface.

In the coating methods of the present invention, a layer of insulation is applied over at least a portion of an inner helical surface of each coil turn disposed toward the helix lumen, whereby at least a portion of an outer helical surface of each coil turn is uninsulated. The methods of applying the insulating material can be undertaken when the coil 37 is a separate piece part, that is, prior to attachment of the coil 37 to the lead body. This approach may be necessary when the fixation helix is adapted to be advanced from a cavity or chamber in the distal end of the lead body as described above. Alternatively, the methods of applying the insulating material can be undertaken after the coil 37 is affixed to the lead body to extend distally in the manner depicted in the fixed helix pacing lead depicted in FIG. 2. For convenience, it will be assumed that the methods of applying the insulating material are practiced to complete the fabrication of the fixation helix 25 as a piece part to be attached to the lead body and the distal end of an electrical conductor in the lead body.

Figure 5:
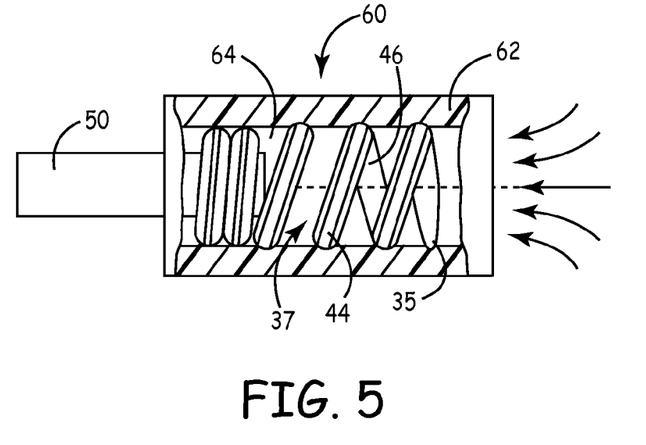
FIG. 5 is a plan view of the distal fixation helix of FIGS. 3 and 4 fitted within a lumen of a masking tube during the deposition of an insulating coating over the inner helical surface of the turns of the fixation helix.
Figure 6:
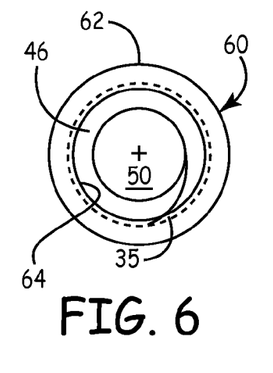
FIG. 6 is an end view of the distal fixation helix of FIGS. 3 and 4 fitted within the lumen of the masking tube during the deposition of the insulating coating.

Turning to FIGS. 5 and 6, a masking tube 60 having a tube wall 62, a tube lumen 64, a tube length at least as long as the coil 37, and a masking tube lumen diameter correlated with the helix outer diameter OD is provided. An interference fit between the outer helical surface of the wire coil 37 and the masking tube lumen diameter is preferred. The masking tube 60 is preferably formed of a flexible polymer material, e.g., silicone rubber, that stretches to be receive the coil 37. In this way, the coil 37 fits into the masking tube lumen 64 providing a masked outer helical surface 44 of each coil turn in intimate contact with the tube wall 62 and an inner helical surface 46 exposed to coating with the insulating material. Preferably, at least a portion of the adjacent coil turns that face one another are exposed within the masking tube lumen 64.

Then, a polymer from among the group consisting of silicone rubber, parylene, polyurethane, polyacrylate, polymethacrylate, polyester, polyamide, polyether, polysiloxane, and polyepoxide is deposited upon the inner helical surface of each coil turn within the masking tube lumen 64. For example, the assembly of the masking tube 60, the coil 37, and the crimp tube 50 are placed in a vacuum chamber of a parylene vacuum deposition system that delivers poly-paraxylylene into the vacuum chamber. A parylene coating is deposited upon the exposed inner helical surface 46 to form the inner helical insulating coating 42.

Figure 7:
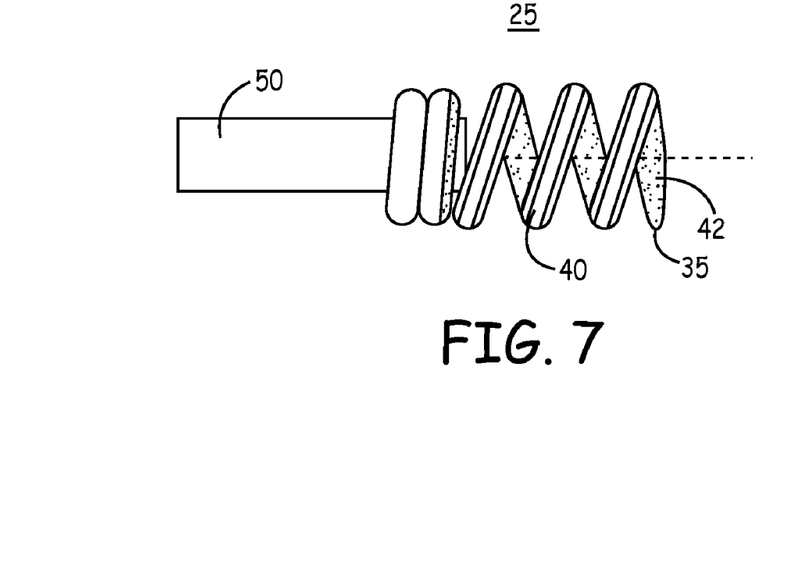
FIG. 7 is a plan view of the distal fixation helix upon removal of the masking tube following deposition of an insulating coating over the inner helical surface of the turns of the fixation helix and showing the exposed pace/sense electrode on the outer helical surface of the turns of the fixation helix.
Figure 8:
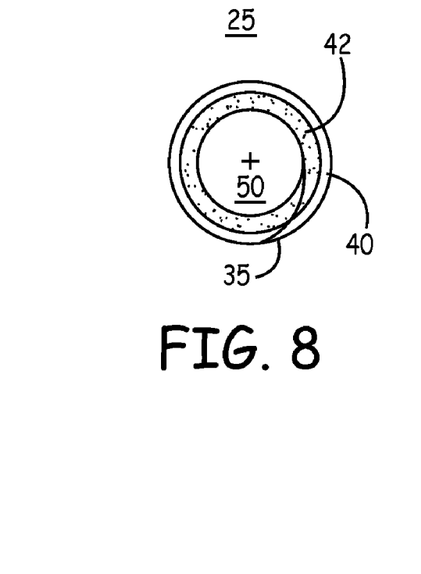
FIG. 8 is an end view of the distal fixation helix of FIG. 7.

The masking tube 60 is removed after the coating has solidified, and resulting fixation helix 25 shown in FIGS. 7 and 8 now has an exposed, uninsulated outer helical electrode 40 in the area of the masked outer helical surface 44 and an insulating coating 42 over the exposed inner helical surface 46. The fixation helix 25 is then assembled to the lead body in accordance with the methods employed to fabricate any particular electrical medical lead, e.g., the pacing lead 20 of FIG. 2. As noted above, the process illustrated in FIGS. 3-8 can be applied to a coil 37 that is already affixed to the distal end of a lead body, particularly if the coil 37 is not retractable into and extendable from a distal cavity of the lead body.

Figure 9:
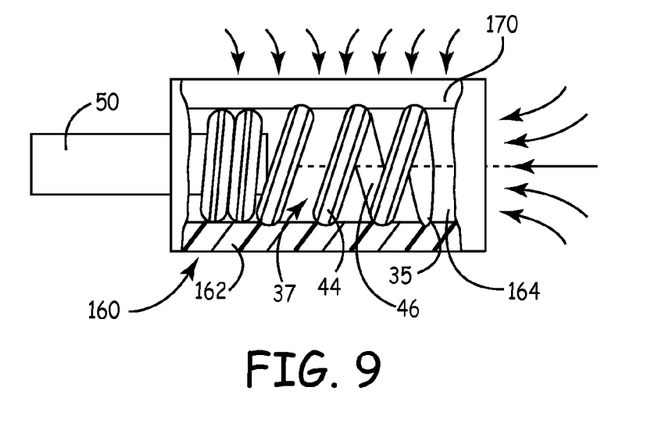
FIG. 9 is a plan view of a further embodiment of the distal fixation helix fitted within a lumen of a masking tube having an aperture through the tube side wall during the deposition of an insulating coating over the inner helical surface of the turns of the fixation helix and discrete areas of the outer helical surface.
Figure 10:
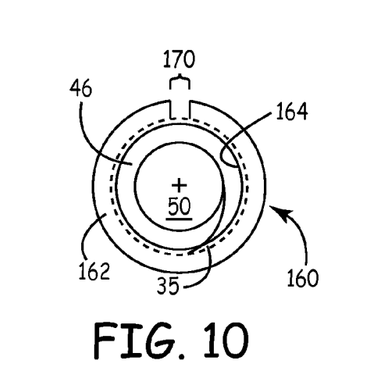
FIG. 10 is an end view of the distal fixation helix of FIG. 9 fitted within the lumen of the masking tube during the deposition of the insulating coating.
Figure 11:
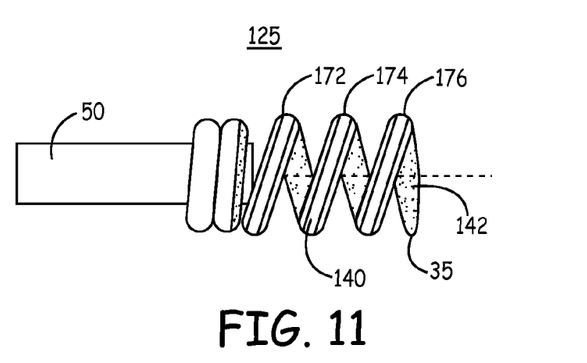
FIG. 11 is a plan view of the distal fixation helix upon removal of the masking tube following deposition of an insulating coating over the inner helical surface of the turns of the fixation helix and showing the exposed pace/sense electrode on the outer helical surface of the turns of the fixation helix.
Figure 12:
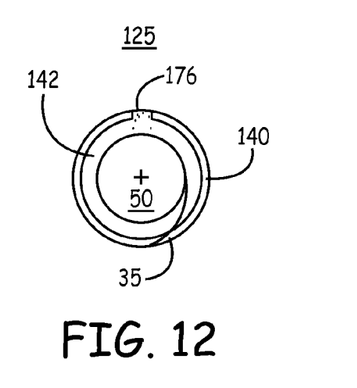
FIG. 12 is an end view of the distal fixation helix of FIG. 11.

An alternative fabrication method is depicted in FIGS. 9 and 10 that results in the fixation helix 125 depicted in FIGS. 11 and 12, having an interrupted outer helical electrode 140. In this method, the masking tube 160 is formed having a tube wall 162, a tube lumen 164, a tube length at least as long as the coil 37, and a masking tube lumen diameter correlated with the helix outer diameter OD is provided. An elongated aperture 170 is provided through the tube wall 162 that exposes one or more area or portion of the outer surface 44. In the depicted example, the aperture 170 comprises a slit through the tube wall 162 extending substantially the length of the masking tube 160. The masking tube 160 is dimensioned to provide an interference fit between the outer helical surface 44 of the wire coil 37 and the masking tube wall 162. Again, the masking tube 160 is preferably formed of a flexible polymer material, e.g., silicone rubber, that stretches to be receive the coil 37. In this way, the coil 37 fits into the masking tube lumen 164 providing a masked outer helical surface 144 of each coil turn in intimate contact with the tube wall 162 and an exposed inner helical surface 146 exposed to coating with the insulating material. In addition, a portion of each coil turn is exposed through the aperture 170.

In this method, the parylene (or other polymer) coating is applied as described above into the masking tube lumen 164 and is also applied through the aperture 170 as shown in FIGS. 9 and 10. Again, the masking tube 160 is removed, and the resulting coating material extends around the circumference of the wire 36 of the coil turn crossing the aperture 170 in bands 172, 174, 176.

As shown in FIGS. 11 and 12, the resulting fixation helix 125 has an outer helical electrode 140 that is interrupted by the insulating layer bands 172, 174, 176. The number and surface area of bands 172, 174, 176 can be selectively controlled by selection of the length and width of the aperture 170 and by inclusion of further apertures around the circumference of the masking tube 160. In this way, the resulting surface area of the outer helical electrode 140 can be tailored as found suitable for any intended implantation site.

Thus, following fixation in the myocardium, the exposed outer helical electrodes 40 and 140 are directed toward viable, excitable myocardial cells, and battery energy can be conserved due to as pacing energy is directed away from traumatized cells within the helix lumen and between the spiral coil turns. The exposed electrode surface area can be substantially reduced even for a small diameter fixation helix to achieve an optimal impedance due to the outward orientation of the outer helical electrode surface that avoids delivering stimulation energy to traumatized tissue or myocardial cells within the helix lumen or between the adjacent facing surfaces of the coil turns.

In preferred embodiments, the helix is formed of platinum metal or a platinum alloy and the uninsulated helical outer surface is coated with a coating selected the a coating selected from the group consisting of titanium nitride, iridium oxide, platinum black and carbon nanotubes.

Preferred embodiments of the present invention also include applying a steroid coating on fixation helices 25 and 125 that is applied during or following their formation as described above. In this regard, one preferable way of applying the steroid coating would be to molecularly bond the steroid with the insulating material, e.g., a silicone rubber or a polyurethane compound, that is deposited to form the coating. Alternatively, the steroid may be deposited onto the coating of insulating material before removing the masking tube 60 or 160. Suitable steroids include derivatives of dexamethasone, such as the water-soluble steroid dexamethasone sodium phosphate, beclomethasone diproprionate, and dexamethasone acetate.

Conclusion

All patents and publications identified herein are incorporated herein by reference in their entireties.

While particular embodiments of the invention have been disclosed herein in detail, this has been done for the purposes of illustration only, and is not intended to limit the scope of the invention as defined in the claims that follow. It is to be understood that various substitutions, alterations, or modifications can be made to the disclosed embodiments without departing from the spirit and scope of the claims. The above described implementations are simply those presently preferred or contemplated by the inventors, and are not to be taken as limiting the present invention to the disclosed embodiments. It is therefore to be understood, that within the scope of the appended claims, the invention may be practiced otherwise than as specifically described without actually departing from the spirit and scope of the present invention.

We claim:

1. An electrical medical lead adapted to be implanted within the body at an implantation site to conduct electrical stimulation from an implantable stimulator to the site and to conduct electrical signals of the body from the site to the implantable or external stimulator comprising:

an elongated lead body extending from a lead body proximal end to a lead body distal end;

a lead connector element at the lead body proximal end;

a lead conductor enclosed within the lead body and electrically coupled to the first lead connector element;

an active fixation helix attached to the lead body distal end electrically coupled to the lead conductor, the fixation helix comprising a plurality of coil turns wound about a helix lumen, the fixation helix extending distally from a helix attachment end to a helix tip shaped to penetrate body tissue when the helix is screwed into body tissue to secure fixation to the implantation site, the plurality of coil turns each having a coil outer diameter defining a helix outer diameter and a coil inner diameter defining a helix lumen diameter; and a continuous coating of insulation extending without interruption from the helix attachment end to the helix tip covering only an inner helical surface of each of the coil turns and disposed to face inward toward the helix lumen;

wherein at least a portion of an outer helical surface extending along the helix outer diameter each coil turn is uninsulated and facing opposite the inner helical surface covered by the layer of insulation.

2. The electrical medical lead of claim 1, wherein the fixation helix comprises a plurality of coil turns wound with a constant pitch and inner and outer diameter from the helix attachment end to the helix tip thereby defining a space between facing surfaces of adjacent coil turns, and the layer of insulation covers at least portions of the facing surfaces.

3. The electrical medical lead of claim 2, wherein the helix is formed of platinum metal or a platinum alloy and the uninsulated helical outer surface is coated with a coating selected from the group consisting of titanium nitride, iridium oxide, platinum black, and carbon nanotubes.

4. The electrical medical lead of claim 2, wherein the uninsulated helical outer surface is in a continuous band extending substantially between the point of attachment to the helix tip.

5. The electrical medical lead of claim 4, wherein the uninsulated helical outer surface has a surface area in the range of about 10% to about 50% of the total surface area.

6. The electrical medical lead of claim 2, wherein the uninsulated helical outer surface is interrupted by the insulating layer applied along the helical outer surface between the point of attachment and the helix tip.

7. The electrical medical lead of claim 6, wherein the uninsulated helical outer surface has a surface area in the range of about 10% to about 50% of the total surface area.

8. The electrical medical lead of claim 1, wherein the helix is formed of platinum metal or a platinum alloy and the uninsulated helical outer surface is coated with a coating selected from the group consisting of titanium nitride, iridium oxide, platinum black, and carbon nanotubes.

9. The electrical medical lead of claim 1, wherein a steroid selected from the group consisting of derivatives of dexamethasone, dexamethasone sodium phosphate, beclomethasone diproprionate, and dexamethasone acetate is applied onto or incorporated into at least a portion of the insulating layer.

10. An electrical medical lead adapted to be implanted within the body at an implantation site to conduct electrical stimulation from an implantable stimulator to the site and to conduct electrical signals of the body from the site to the implantable or external stimulator comprising:

an elongated lead body extending from a lead body proximal end to a lead body distal end;

a lead connector element at the lead body proximal end;

a lead conductor enclosed within the lead body and electrically coupled to the first lead connector element;

an active fixation helix attached to the lead body distal end electrically coupled to the lead conductor, the fixation helix comprising a conductive wire formed into a coil comprising a plurality of coil turns wound about a helix lumen, the fixation helix extending distally from a helix attachment end to a helix tip shaped to penetrate body tissue when the helix is screwed into body tissue to secure fixation to the implantation site, the conductive wire having a circumferential surface and each coil turn formed by the conductive wire having a coil outer diameter defining a helix outer diameter and a coil inner diameter defining a helix lumen diameter;

a coating of insulation applied to the circumferential surface of the conductive wire, the insulating layer extending only part way around the circumferential surface of the conductive wire to cover the coil inner diameter without covering the coil outer diameter directly opposite the covered coil inner diameter of each coil turn, wherein the insulating layer covers an inner helical surface disposed toward the helix lumen of each coil turn and an outer helical surface opposite the insulated inner helical surface extending along the helix outer diameter of each coil turn is uninsulated, and the uninsulated outer helical surface functions as an outer helical electrode disposed toward body tissue away from the helix.

11. The electrical medical lead of claim 10, wherein the fixation helix comprises a plurality of coil turns wound with a constant pitch and inner and outer diameter from the helix attachment end to the helix tip thereby defining a space between facing surfaces of adjacent coil turns, and the layer of insulation covers at least portions of the facing surfaces.

12. The electrical medical lead of claim 10, wherein the helix is formed of platinum metal or a platinum alloy and the uninsulated helical outer surface is coated with a coating selected from the group consisting of titanium nitride, iridium oxide, platinum black, and carbon nanotubes.

13. The electrical medical lead of claim 10, wherein the uninsulated helical outer surface is in a continuous band extending substantially between the point of attachment to the helix tip.

14. The electrical medical lead of claim 10, wherein the uninsulated helical outer surface has a surface area in the range of about 10% to about 50% of the total surface area.

15. An electrical medical lead adapted to be implanted within the body at an implantation site to conduct electrical stimulation from an implantable stimulator to the site and to conduct electrical signals of the body from the site to the implantable or external stimulator comprising:
   an elongated lead body extending from a lead body proximal end to a lead body distal end;
   a lead connector element at the lead body proximal end;
   a lead conductor enclosed within the lead body and electrically coupled to the first lead connector element;
   an active fixation helix attached to the lead body distal end electrically coupled to the lead conductor,
     the fixation helix comprising a plurality of coil turns wound about a helix lumen, the fixation helix extending distally from a helix attachment end to a helix tip shaped to penetrate body tissue when the helix is screwed into body tissue to secure fixation to the implantation site,
   the fixation helix having an outer surface and an inner surface forming a helix lumen;
   each coil turn of the fixation helix being formed from a substantially circular wire having a circumferential surface area; and
   a coating of insulation extending without interruption from the helix attachment end to the helix tip, the insulation layer covering a substantial portion of the circumferential surface area of the wire forming each coil turn to define a portion of the circumferential surface area of the wire that is uninsulated so as to cover only the helix inner surface and leave an exposed helix outer surface, wherein only the exposed helix outer surface functions as an electrode disposed toward body tissue away from the helix lumen.

16. The electrical medical lead of claim 15, wherein the fixation helix comprises a plurality of coil turns wound with a constant pitch and inner and outer diameter from the helix attachment end to the helix tip thereby defining a space between facing surfaces of adjacent coil turns, and the layer of insulation covers at least portions of the facing surfaces.

17. The electrical medical lead of claim 15, wherein the helix is formed of platinum metal or a platinum alloy and the uninsulated helical outer surface is coated with a coating selected from the group consisting of titanium nitride, iridium oxide, platinum black, and carbon nanotubes.

18. The electrical medical lead of claim 15, wherein the uninsulated helical outer surface is in a continuous band extending substantially between the point of attachment to the helix tip.

19. The electrical medical lead of claim 15, wherein the uninsulated helical outer surface has a surface area in the range of about 10% to about 50% of the total surface area.

* * * * *